United States Patent
Diebold et al.

(10) Patent No.: US 6,261,292 B1
(45) Date of Patent: Jul. 17, 2001

(54) THREADED PIN

(75) Inventors: Francois Patrice Diebold, Nancy (FR); Ramon Viladot Perice, Barcelona (ES); Sylvia Resch, Karlshamm (SE); Greta Dereymaeker, Oud-Heverlee (BE); Beat Hintermann, Richen (CH); Nikolaus Wülker, Hannover (DE)

(73) Assignee: European Foot Platform, Nancy (FR)

( * ) Notice: Subject to any disclaimer, the term of this patent is extended or adjusted under 35 U.S.C. 154(b) by 0 days.

(21) Appl. No.: 09/495,950

(22) Filed: Feb. 2, 2000

(30) Foreign Application Priority Data

Feb. 2, 1999 (FR) .................................................. 99 01112

(51) Int. Cl.$^7$ .................................................. A61B 17/58
(52) U.S. Cl. .............................. 606/73; 606/72; 411/307; 411/415
(58) Field of Search .................................. 606/65, 72, 73; 623/16.11, 17.11; 411/415, 423, 426, 307, 310, 311, 411

(56) References Cited

U.S. PATENT DOCUMENTS

| | | | |
|---|---|---|---|
| 3,466,748 | * 9/1969 | Christensen | 606/73 |
| 4,175,555 | * 11/1979 | Herbert | 606/73 |
| 4,463,753 | * 8/1984 | Gustilo | 606/73 |
| 4,978,350 | * 12/1990 | Wagenknecht | 606/72 |
| 5,019,079 | * 5/1991 | Ross | 606/72 |
| 5,562,672 | 10/1996 | Huebner et al. | 606/73 |
| 6,001,101 | * 12/1999 | Augagneur et al. | 606/73 |

FOREIGN PATENT DOCUMENTS

| | | | |
|---|---|---|---|
| 2760628 | 9/1998 | (FR) | A61B/17/58 |
| WO95/15727 | 6/1995 | (WO) | A61B/17/58 |
| WO 97/10767 | 3/1997 | (WO) | A61B/17/86 |

OTHER PUBLICATIONS

D.M. Belloli et al., Abstract presented at the 9th Annual Conference of the Engineering in Medicine and Biology Society/IEEE Meeting, Nov. 13–16, 1987, entitled "a Biomechanical Comparison Between Herbert and 4.0 Cancellous Screws."

* cited by examiner

*Primary Examiner*—Pedro Philogene
(74) *Attorney, Agent, or Firm*—Millen, White, Zelano & Branigan, P.C.

(57) ABSTRACT

The invention relates to a threaded pin for holding together pieces of a fractured bone. The pin comprises a body having a distal end and a proximal end. The distal end has a first thread presenting crests and the proximal end has a second thread presenting crests. The first thread and the second thread being spaced apart by a smooth portion. The first and second threads are such that the pitch X of the first thread and the pitch Y of the second thread both decrease from the distal end ($X_1$, $X_2$, $Y_1$, $Y_2$) towards the proximal end ($X_n$, $X_{n-1}$; $Y_n$, $Y_{n-1}$). The diameter d of the crests of the first thread and the diameter D of the crests of the second thread both increase from the distal end ($d_1$, $d_2$; $D_1$, $D_2$) towards the proximal end ($d_n$, $d_{n-1}$; $D_n$, $D_{n-1}$), and the values are such that:

$X_1 > X_2 > X_{n-1} > X_n > Y_1 > Y_2 > Y_{n-1} > Y_n$ and $D_n > D_{n-1} > D_2 > D_1 > d_n > d_{n-1} > d_2 > d_1$.

The invention is applicable to repairing bones.

11 Claims, 2 Drawing Sheets

THREADED PIN

SUMMARY OF TIE INVENTION

The present invention relates to a threaded pin for holding together pieces of a bone that have been separated by a fracture, and more particularly the invention relates to a pin enabling compression to be applied to two bone fragments regardless of the level at which cutting takes place in a case of osteotomy.

In order to heal a bone fracture, it is desirable to compress the fracture in such a manner as to press together the surfaces of the fracture.

A screw with a threaded head is already known for the osteosynthesis of bone fragments. For example, French patent application FR-A-2 760 628 describes a threaded-head screw for the osteosynthesis of bone fragments, where the screw comprises a distal portion provided with a cylindrical thread and a proximal portion or head provided with a conical thread of diameter that increases towards the proximal end of said screw. The pitch P of the conical thread of the proximal portion is smaller than the pitch P' of the cylindrical thread on the distal portion. The distal portion and the proximal portion are spaced apart by a smooth portion. The pitches P and P' are constant.

U.S. Pat. No. 5,562,672 describes a screw for holding together pieces of a bone that have been separated by a fracture, the screw comprising a distal or control portion and a proximal or rear portion. The screw has a thread which extends from the distal end to the proximal end, a crest being formed on said thread. The radius of the crest is greater close to the proximal end and smaller close to the distal end. The pitch measured between corresponding points on consecutive thread crests decreases continuously from a greater value close to the distal end towards a smaller value close to the proximal end.

Prior art pins (smooth, unthreaded and cylindrical) suffer from several drawbacks. They do not ensure that there is no skidding on the piece of bone while the pin is being inserted. Nor do they make it possible to compress the two pieces of bone sufficiently on either side of the fracture. Finally, they do not make it possible to avoid the pin breaking under normal conditions of use.

An object of the invention is thus to mitigate the drawbacks of prior art pins.

Upon further study of the specification and appended claims, further objects and advantages of this invention will become apparent to those skilled in the art.

To this end, the invention provides a pin comprising a body with a distal end and a proximal end, wherein the distal end has a first thread presenting crests, the proximal end has a second thread presenting crests, the first thread and the second thread being spaced apart by a smooth portion, and the first and second threads being such that the pitch X of the first thread and the pitch Y of the second thread both decrease from the distal end ($X_1$, $X_2$; $Y_1$, $Y_2$) towards the proximal end ($X_n$, $X_{n-1}$; $Y_n$, $Y_{n-1}$), and wherein the diameter d of the crests of the first thread and the diameter D of the crest of the second thread both increase from the distal end ($d_1$, $d_2$; $D_1$, $D_2$) towards the proximal end ($d_n$, $d_{n-1}$; $D_n$, $D_{n-1}$), with the values being such that $X_1 > X_2 > X_{n-1} > X_n > Y_1 > Y_2 > Y_{n-1} > Y_n$ and $D_n > D_{n-1} > D_2 > D_1 > d_n > d_{n-1} > d_2 > d_1$.

In addition, the pin of the invention is such that preferably:

the distal portion has a sharp tip at its end;

the diameter di has a value lying in the range 1 mm to 20 mm, i.e., $1 \text{ mm} \leq d_1 \leq 20 \text{ mm}$;

the length from the distal end to the proximal end lies in the range 5 mm to 50 mm;

the proximal portion is terminated by a cylindrical body; or the proximal portion is terminated by a cylindrical body having a significant decrease in diameter.

BRIEF DESCRIPTION OF THE DRAWINGS

The following description with reference to the accompanying drawings given as non-limiting examples makes it possible to understand how the invention can be put into practice. Various other features and attendant advantages of the present invention will be more filly appreciated as the same becomes better understood when considered in conjunction with the accompanying drawings, in which like reference characters designate the same or similar parts throughout the several views, and wherein.

DETAILED DESCRIPTION OF THE DRAWINGS

Figure 1:
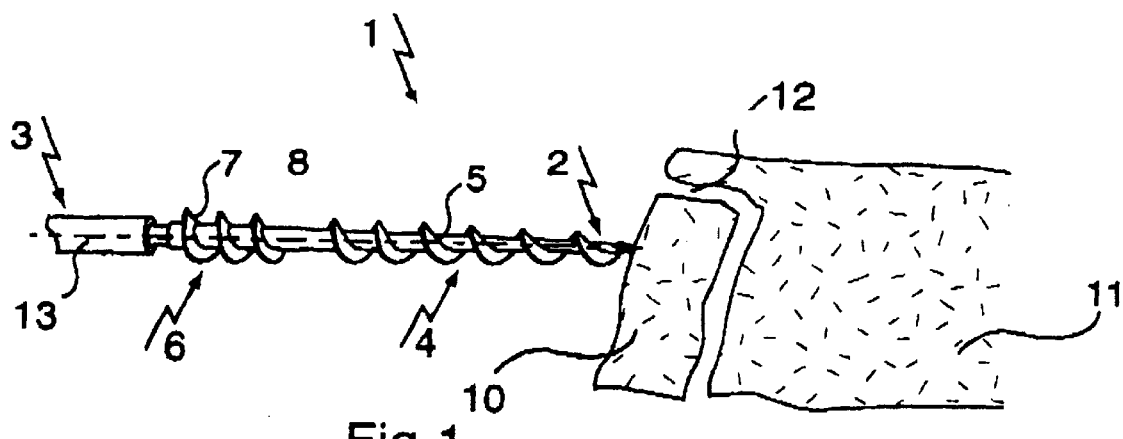
FIG. 1 is a diagram of a pin of the invention in place prior to being inserted in the piece of bone.

The pin 1 of the invention has a distal end 2 and a proximal end 3. It is generally conical in shape. The distal end 2 has a first thread 4 presenting crests 5. The proximal end 3 has a second thread 6 presenting crests 7. The first thread 4 and the second thread 6 are separated by a smooth portion 8. The distal end 2, the smooth portion 8, and the proximal end 3 form a body 9 which, ignoring the threads 4 and 6, is generally conical in shape, with the tip of the cone forming the distal portion 2. The first thread 4 has a pitch X which is not constant and which decreases going from the distal end 2 towards the proximal end 3. Thus, the pitch $X_1$ between two contiguous crests $5_1$ and $5_2$ is greater than the pitch $X_2$ between the following two crests $5_2$ and $5_3$, the pitch $X_n$ between $5_{n-1}$ and $5_n$ being less than the pitch $X_{n-1}$ between crests $5_{n-2}$ and crest $5_{n-1}$. It is thus possible to write $X_n < X_{n-1}$.

Similarly, the second thread 6 has a pitch Y which is not constant and which decreases from the distal end 2 towards the proximal end 3. Thus, the pitch $Y_1$ between two contiguous crests $7_1$ and $7_2$ is greater than the pitch $Y_2$ between the following two crests $7_2$ and $7_3$, the pitch $Y_n$ between $7_{n-1}$ and the crest $7_n$ being less than the pitch $y_{n-1}$ between the crest $7_{n-2}$ and the crest $7_{n-1}$. It is thus possible to write $Y_n < Y_{n-1}$.

The diameters d of the crests of the first thread 4 and the diameters D of the crests of the second thread 6 increase from the distal end 2 towards the proximal end 3. Thus, the diameter $d_n$ of the crest $5_n$ is greater than the diameter $d_{n-1}$ of the crest $5_{n-1}$ and the diameter $D_n$ of the crest $7_n$ is greater than the diameter $D_{n-1}$ of the crest $7_{n-1}$ and $D_{n-1}$ is greater than $d_n$.

Preferably, the distal portion 2 has a sharp tip.

Figure 2:
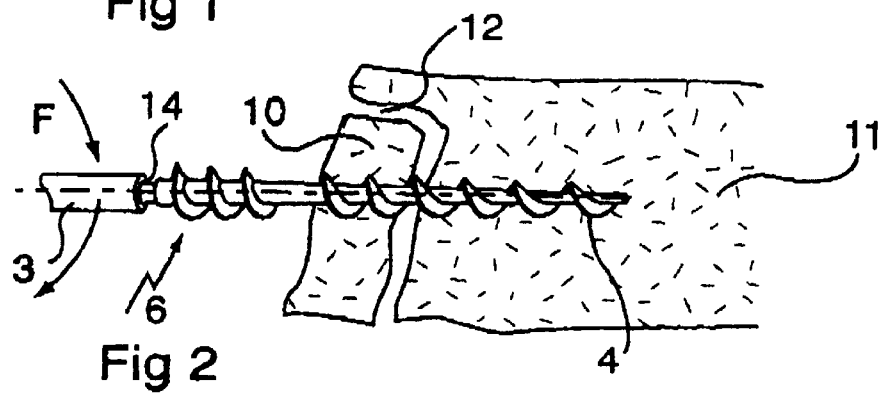
FIG. 2 is a diagram of the FIG. 1 pin at the beginning of its progress into the pieces of bone that are to be moved together.
Figure 3:
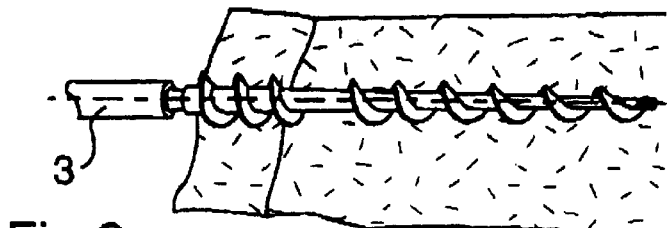
FIG. 3 is a diagram of the FIG. 1 pin after the pieces of bone have been brought together.
Figure 4:
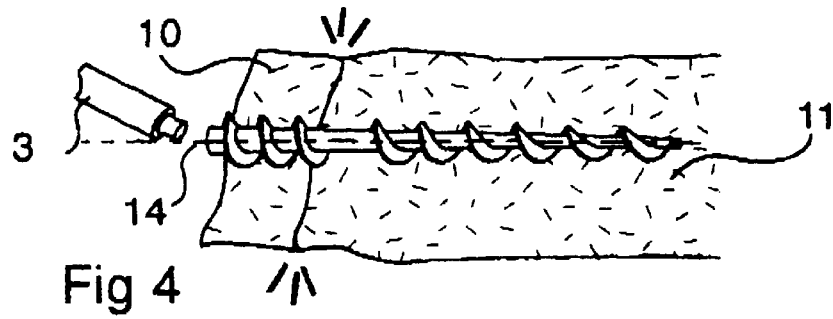
FIG. 4 is a diagram of the FIG. 1 pin in its final position, the pieces of bone being compressed.
Figure 5:
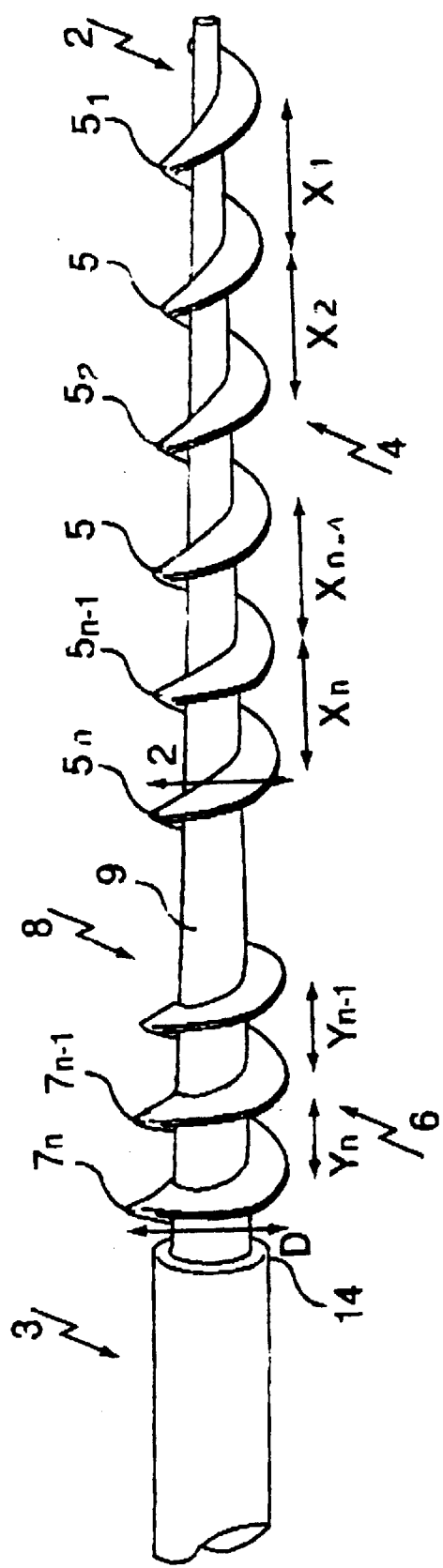
FIG. 5 is a view of the pin of the invention.

As can be seen more particularly in FIGS. 1 to 4, the pin of the invention is designed to move together two pieces of bone 10 and 11 that are separated by a break 12. The pin 1 of the invention is inserted in the broken piece and on insertion of the pin, the sharp tip prevents any skidding over the piece of bone 10. Thereafter the pin 1 is turned (in the direction represented by arrow 1) and on each turn, the distal end 2 having the greater screw pitch $X_1$ progresses more quickly into the piece of bone 10 than does the proximal end 3 having the smaller screw pitch (FIG. 2). The pieces of hi bone 10 and 11 are thus moved towards each other and come into contact with other (FIG. 3). Thereafter, continued turning of the pin I causes the two pieces of bone 10 and 11 to be compressed against each other (FIG. 4).

The smooth portion 9 makes it easier for the pin 1 to slide in translation along the longitudinal axis XX while it is being turned, thereby making it easier to compress the two pieces of bone 10 and 11 together. Furthermore, the diameter between said smooth portion and the end of the thread is greater than a value for ensuring that rupture is avoided under normal conditions of use. For a pin having a maximum diameter of 1.7 mm, the diameter between the smooth portion 9 and the end of the thread is greater than 1.2 mm. This 1.2 mm value is known in the literature as being the optimum value for avoiding rupture of a pin under normal conditions of use.

The value of the diameter $d_1$ lies in the range 1 mm to 20 mm, thus 1 mm$\leq d_1 \leq$20 mm, and the length from the distal end to the proximal end lies in the range 5 mm to 50 mm.

In an embodiment not shown in the figures, the proximal portion 3 is terminated by a cylindrical body; or as in the embodiment shown in the figures, the proximal portion 3 is terminated by a cylindrical body 13 that includes a considerable reduction in diameter, thereby forming a neck 14. This neck 14 enables the proximal portion 3 to be broken off by applying torque perpendicularly to the longitudinal axis XX of the pin (see FIG. 4). It is also possible to cut off the proximal portion 3 using snips.

The length of the region of the first thread is preferably about 60 to 75% of the total combined length of the region of the first thread, the smooth portion, and the region of the second thread (termed "L", represented by 6+9+4 in the drawing). In addition, the length of the region of second thread is preferably about 25 to 40% of the total combined length of the region of the first thread, the smooth portion, and the region of the second thread.

More preferably:

length of first thread 4=⅓ L;

length of second thread 6=⅔ L—1,5 mm;

length of body 9=1,5 mm (this length is preferably fixed regardless of the length of first and second threads).

The preferred lengths of L are 15, 20, 25 mm. However, other lengths are envisaged such as 11, 13, 30, 35 mm. Moreover, $d_1$ is preferably about 1 mm but can vary from about 0.5 to 1.5 mm.

From the foregoing description, one skilled in the art can easily ascertain the essential characteristics of this invention and, without departing from the spirit and scope thereof, can make various changes and modifications of the invention to adapt it to various usages and conditions.

The entire disclosure of all applications, patents and publications, cited above, and of corresponding French application No. 99 01112, filed Feb. 2, 1999, are hereby incorporated by reference.

What is claimed is:

1. A pin comprising:

a body with a distal end and a proximal end, wherein said distal end has a first thread presenting crests, said proximal end has a second thread presenting crests, said first thread and said second thread are spaced apart by a smooth portion, the first and second threads being such that the pitch X of the first thread and the pitch Y of the second thread both decrease from the distal end ($X_1$, $X_2$; $Y_1$, $Y_2$) towards the proximal end ($X_n$, $X_{n-1}$; $Y_n$, $Y_{n-1}$), and wherein the diameters (d) of the crests of the first thread and the diameters (D) of the crest of the second thread both increase from the distal end ($d_1$, $d_2$; $D_1$, $D_2$) towards the proximal end ($d_n$, $d_{n-1}$; $D_n$, $D_{n-1}$), with the values being such that $X_1 > X_2 > X_{n-1} > X_n > Y_1 > Y_2 > Y_{n-1} > Y_n$ and $D_n > D_{n-1} > D_2 > D_1 > d_n > d_{n-1} > d_2 > d_1$.

2. A pin according to claim 1, wherein the distal end has a sharp tip at its end.

3. A pin according to claim 1, wherein the diameter di of the first crest of the first thread has a value whereby 1 mm$\leq d_1 \leq$20 mm.

4. A pin according to claim 1, wherein the length from the distal end to the proximal end is 5 mm to 50 mm.

5. A pin according to claim 1, wherein the proximal end is terminated by a cylindrical body.

6. A pin according to claim 1, wherein the proximal end is terminated by a cylindrical body having a decrease in diameter so as to form a neck.

7. A pin according to claim 4, wherein the diameter di of the first crest of the first thread has a value whereby 1 mm$\leq d_1 \leq$20 mm.

8. A pin according to claim 7, wherein the distal end has a sharp tip at its end.

9. A pin according to claim 8, wherein the diameter di of the first crest of the first thread has a value whereby 1 mm$\leq d_1 \leq$20 mm.

10. A pin according to claim 9, wherein the proximal end is terminated by a cylindrical body.

11. A pin according to claim 10, wherein said cylindrical body exhibits a decrease in diameter so as to form a neck.

* * * * *

UNITED STATES PATENT AND TRADEMARK OFFICE
CERTIFICATE OF CORRECTION

PATENT NO. : 6,261,292 B1
DATED : July 17, 2001
INVENTOR(S) : Diebold et al.

It is certified that error appears in the above-identified patent and that said Letters Patent is hereby corrected as shown below:

Title page,
Inventor, reads "Francois Patrice" should read -- Patrice Francois --;

Column 4, claim 3,
Line 1, reads "di" should read -- $d_1$ --;

Column 4, claim 7,
Line 1, reads "di" should read -- $d_1$ --;

Column 4, claim 9,
Line 1, reads "di" should read -- $d_1$ --.

Signed and Sealed this

Second Day of April, 2002

*Attest:*

JAMES E. ROGAN
*Attesting Officer*     *Director of the United States Patent and Trademark Office*